United States Patent [19]

Detsch

[11] Patent Number: 5,073,114
[45] Date of Patent: Dec. 17, 1991

[54] BONE GROWING METHOD AND COMPOSITION

[76] Inventor: Steven G. Detsch, 4115 The Hill Rd., Bonita, Calif. 92002

[21] Appl. No.: 419,377

[22] Filed: Oct. 10, 1989

Related U.S. Application Data

[63] Continuation-in-part of Ser. No. 159,126, Feb. 23, 1988, Pat. No. 4,911,641.

[51] Int. Cl.⁵ .............................................. A61K 6/03
[52] U.S. Cl. .................................... 433/228.1; 623/16
[58] Field of Search ........................ 623/16; 433/228.1

[56] References Cited

U.S. PATENT DOCUMENTS

| | | | |
|---|---|---|---|
| 4,610,692 | 9/1986 | Eitenmuller et al. | 623/16 |
| 4,623,553 | 11/1986 | Ries et al. | 623/16 |
| 4,738,623 | 4/1988 | Driskell | 433/228.1 |
| 4,932,973 | 6/1990 | Gendcer | 623/16 |

Primary Examiner—V. Millin
Attorney, Agent, or Firm—Michael W. York

[57] ABSTRACT

A method and composition for promoting the growth of bone that are particularly useful in treating bony defects in the human jaw. The method includes surgically exposing the bony defect, cleaning the defect and adjacent teeth, and implanting the composition in the bony defect. The bone growing composition includes two sizes of Hydroxyapatite for supporting the growth of new bone, Tetracycline for its antibiotic effect, freeze dried decalcified human bone for promoting bone growth, and Fibronectin for promoting connective tissue generation and for jelling the bone growing composition.

21 Claims, 3 Drawing Sheets

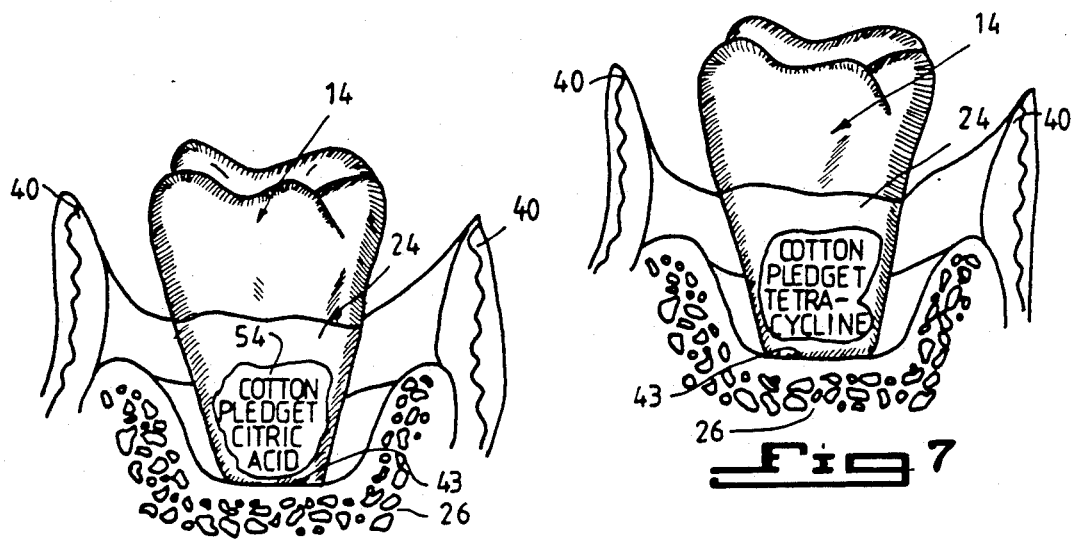
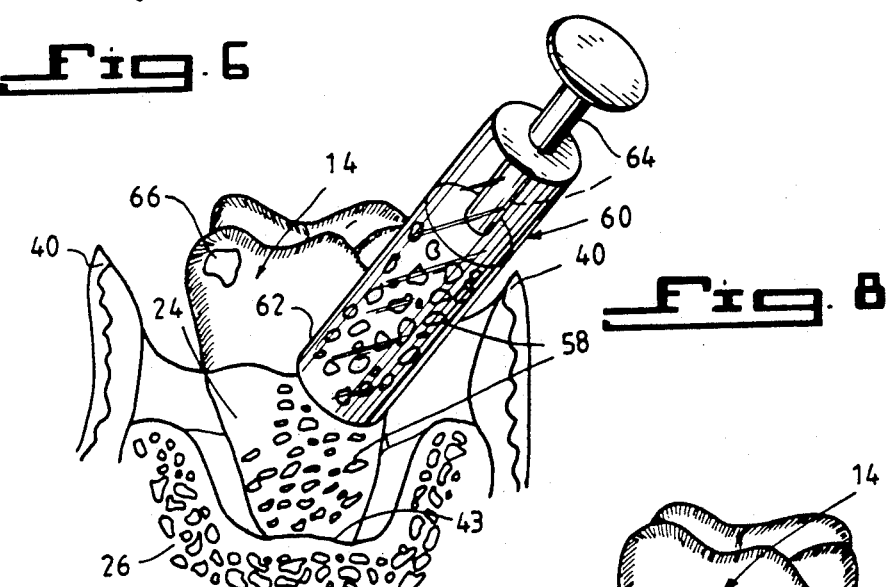
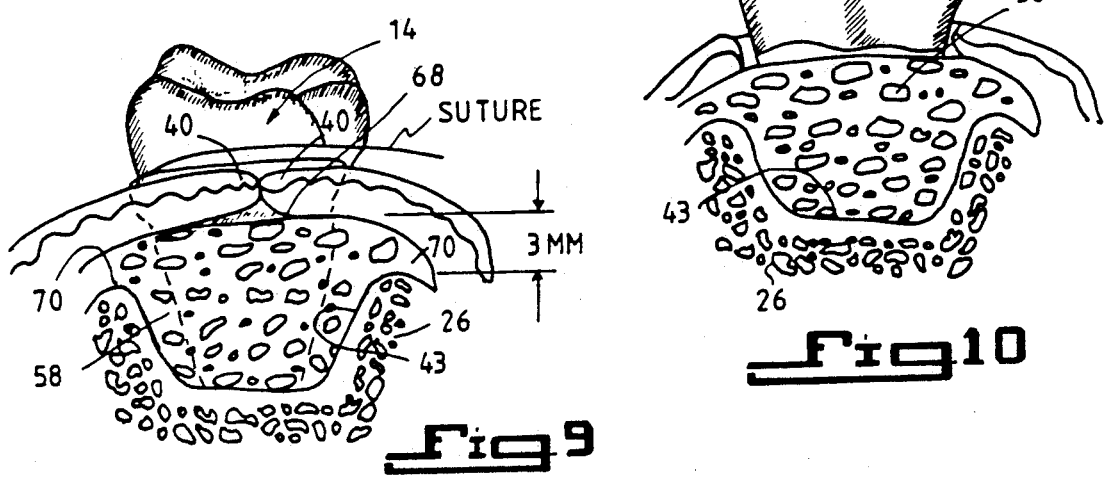

BONE GROWING METHOD AND COMPOSITION

CROSS REFERENCE TO RELATED APPLICATION

This application is a continuation in part of U.S. patent application Ser. No. 07/159,126 filed Feb. 23, 1988, now U.S. Pat. No. 4,911,641.

BACKGROUND OF THE INVENTION

It has been known for a long time that broken bones in man or in animals will heal themselves or grow together if the broken pieces are relatively intact and if they are located closely adjacent each other so that the broken portions are in appropriate contact with each other. This occurs because new bone grows to fill the joint between the broken portions so that the bone portions are reunited and a single united bone results.

This bone growth does not occur if the bone at the location where the bone is broken is no longer present due to fragmentation of the bone from the same blow or other accident that caused the broken bone. In such instances, bone does not grow to fill the gap created between the broken bone portions and the bone parts will not be reunited. Some success has occurred in overcoming this lack of bone growth, by inserting another piece of bone or the like between the broken and damaged portions of the bone. This bone growth appears to occur as a result of new bone growing over the bone implant.

Although, bone has been successfully used as a bone graft material in the past, there are a number of problems associated with its use. One of these problems is related to the somewhat limited availability of bone as a graft material. This can be traced to the limited donors of bone and also to problems associated with the storage of the bone. In this connection, it should be noted that the proper storage of bone requires that it be sterilized and maintained in a sterile condition until it is used. One method of accomplishing this has been to seal the bone inside an airtight glass tube and to then expose the bone and the glass container to a high dose of radiation. This radiation could come from a Cobalt-60 radiation source or other radiation source. This need for radiation itself is a possible problem since a radiation facility is required and the radiation may alter the bone's ability to have new bone form around it.

One area that is subject to important bone loss is the mouth. Bone loss can occur in the mouth from various causes including trauma. However, the most important causes are from periodontal disease and from the extraction or loss of teeth that causes the surrounding bone to be absorbed or to receed. This loss of bone is important since it can result in the loss of teeth and/or can prevent the suitable use of replacement or artificial teeth. The loss of bone in the mouth is also significant since this occurs in a comparatively large number of people in comparison to the loss or destruction of bone in other portions of the body. The regeneration of bone in the mouth presents physical problems that are usually not present outside the mouth.

Attempts have been made to replace lost bone in the mouth. An example of such an attempt is set forth in U.S. Pat. No. 3,913,229 and involves the use of calcium phosphate as a material to support the growth or regeneration of new tissue and bone. These attempts have not been entirely successful and have not resulted in the desired bone regeneration and reattachment of the regenerated bone to the teeth through an appropriate fiber ligament. This bone growing method and composition overcomes many previous problems and provides improved results. This method and composition is also not restricted to use in the mouth.

SUMMARY OF THE INVENTION

This invention relates to bone growing methods and compositions and more particularly to bone growing methods and compositions that are particularly useful in the mouth.

It is accordingly an object of the invention to provide a bone growing method and composition that assist in the growth of bone.

It is an object of the invention to provide a bone growing method and composition that effectively promote the growth of bone.

It is an object of the invention to provide a bone growing method and composition that are easy to use.

It is also an object of the invention to provide a bone growing method and composition that require no special instruments.

It is an object of the invention to provide a bone growing method and composition that are particularly suited for use in a confined area such as the mouth.

It is an object of the invention to provide a bone growing method and composition that are particularly useful for treating bone loss in the mouth.

It is also an object of the invention to provide a bone growing method and composition that are particularly useful in treating the effects of periodontal disease.

It is also an object of the invention to provide a bone growing method and composition that are particularly useful for successive treatments.

It is an object of the invention to provide a bone growing method and composition that are capable of restoring a greater amount of bone loss.

It is an object of the invention to provide a bone growing method and composition that are particularly useful for restorative cosmetic purposes in the mouth.

It is an object of the invention to provide a bone growing method and composition that are suited for use adjacent to teeth in the mouth.

It is an object of the invention to provide a bone growing method and composition that are useful in reattaching bone to teeth in the mouth.

The invention provides a method of promoting the growth of bone in a living creature that includes providing a graft composition, surgically operating to expose living bone, inserting the graft composition adjacent the living bone and surgically covering the previously exposed living bone and the adjacently located graft composition. The invention also includes the graft composition used in the bone growing method. The invention is particularly useful in replacing bone in the mouth of a human being.

BRIEF DESCRIPTION OF THE DRAWINGS

The invention will be hereinafter more fully described with reference to the accompanying drawings in which:

FIG. 6 is a sectional view of the structure set forth in FIGS. 2 through 5 illustrating a further step in the practice of the method of the invention and the use of the composition of the invention;

FIG. 7 is a sectional view of the structure set forth in FIGS. 2 through 6 illustrating a further step in the practice of the method of the invention and the use of the composition of the invention;

FIG. 8 is a sectional view of the structure set forth in FIGS. 2 through 7 illustrating a further step in the practice of the method of the invention and the use of the composition of the invention;

FIG. 9 is a sectional view of the structure set forth in FIGS. 2 through 8 illustrating a further step in the practice of the method of the invention and the use of the composition of the invention;

FIG. 10 is a sectional view of the structure set forth in FIGS. 2 through 9 illustrating a step in the healing process associated with practice of the method of the invention and the use of the composition of the invention;

DETAILED DESCRIPTION OF THE PREFERRED EMBODIMENTS

Figure 1:
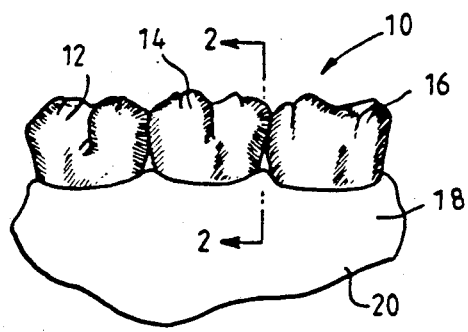
FIG. 1 is an elevational view of a portion of the lower jaw portion of a human mouth.

FIG. 1 is a view of a portion of the human mouth showing the crown portion of the teeth 12, 14, and 16 in side elevation. Surrounding the teeth 12, 14, and 16 is the gingiva 18 and then the adjacent mucosa 20. FIGS. 2 through 16 are sectional views taken substantially on the line 2—2 of FIG. 1.

Figure 2:
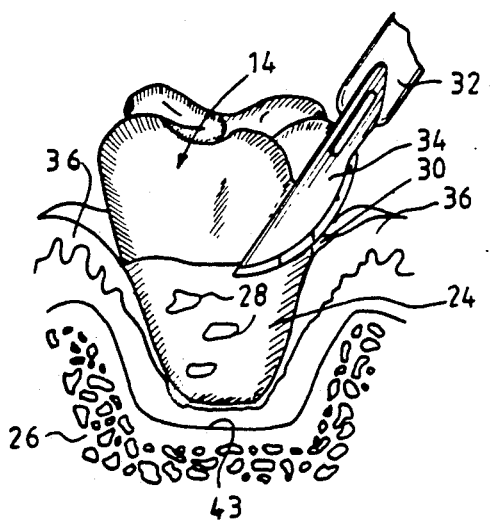
FIG. 2 is a sectional view of a portion of the jaw of the mouth taken substantially on the line 2—2 in FIG. 1 illustrating a step in the practice of the method of the invention and the use of the composition of the invention.

FIG. 2 illustrates the tooth 14 with its tooth crown portion 22 and root portion 24 that is located in bone 26.

As illustrated, the root portion 24 has calculus or tartar 28 attached to it. Also, FIG. 2 illustrates the first step in the practice of the method of the invention and the use of the composition of the invention and that is to make an incision 30 in the gingiva 18 in the area to be treated using a scalpel 32 with a number 15 Bard Parker scalpel blade 34. The popillae and gingival tissue 36 is also retracted in the vicinity of the incision 30 to expose the root portion 24 and the attached calculus 28.

Figure 3:
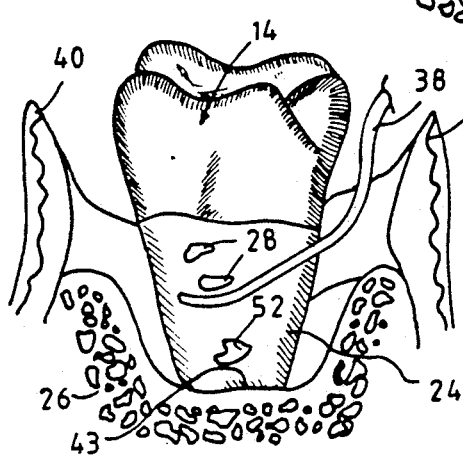
FIG. 3 is a sectional view of the structure illustrated in FIG. 2 illustrating a further step in the practice of the method of the invention and the use of the composition of the invention.

FIG. 3 illustrates the next step in the practice of the method of the invention and in the use of the composition of the invention. As illustrated, the calculus 28 or a substantial amount of the calculus 28 is scraped from the surface of the root portion 24 using a curette 38 known in the art. To accomplish this the gingiva 18 flap edges 40 are retracted. The curette 38 is also used to remove granulation tissue 42 from the flap edges 40. At this time the curette 38 is also used to grossly debride the bony defects such as the defect 43 or an ultrasonic scaler (not shown) could also be used.

Figure 4:
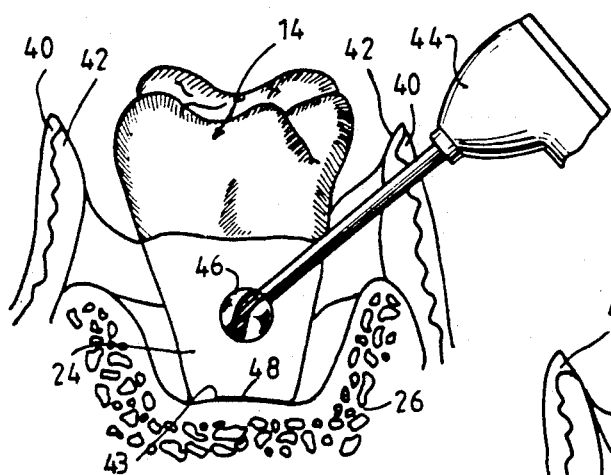
FIG. 4 is a sectional view of the structure set forth in FIGS. 2 and 3 illustrating a further step in the practice of the method of the invention and the use of the composition of the invention.

The next step in the method and the use of the composition of the invention is set forth in FIG. 4. As illustrated, a high speed hand piece 44 is used with a number 6 and a number 1 or 2 round burr 46 to remove residual granulation tissue, epithelia 48 and connective tissue tags down to bone 26.

Figure 5:
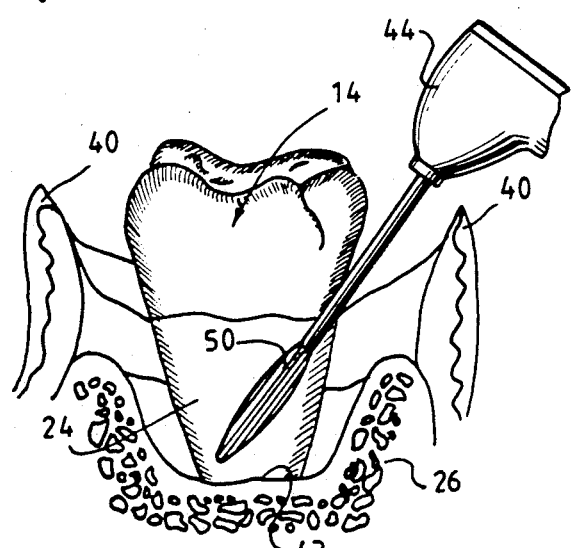
FIG. 5 is a sectional view of the structure set forth in FIGS. 2 through 4 illustrating a further step in the practice of the method of the invention and the us of the composition of the invention.

The next step in the method and the use of the composition of the invention is to use the high speed hand piece 44 with a 12-20 fluted finishing burr 50 to remove surface cementum 52 from the exposed root portion 24 of the tooth 14 as illustrated in FIG. 5. It is important that substantially all of the cementum 52 be removed in this manner from all of the exposed root surface.

The next two steps illustrated in FIGS. 6 and 7 in the method and use of the composition of the invention involve chemical treatment of the surface of the root portion 24 of the tooth 14. In the first chemical step illustrated in FIG. 6 a cotton pledget 54 soaked with citric acid solution is applied to the surface of the root portion 24 of the tooth 14. The citric acid solution is applied to the surface of the root portion 24 through the use of the cotton pledget 54 that is placed against the surface of the root portion 24 for a period of time of substantially one and one-half to substantially three minutes. This treatment with the citric acid solution results in the leaching out of surface calcium and the exposure of decalcified dention. This treatment will encourage subsequent connective tissue attachment to the root portion 24.

As illustrated in FIG. 7, the next step in the chemical treatment portion of the method and the use of the composition of the invention is to chemically treat the surface of the root portion 24 with a Tetracycline solution. As illustrated, this Tetracycline solution is applied to the surface of the root portion 24 by applying a Tetracycline soaked pledget 56 to the surface of the root portion 24 for a period of time between substantially one and one-half to substantially three minutes. The applied solution has substantially a concentration of 1 mg./ml/ of Tetracycline. The effect of this Tetracycline treatment is to further dissolve out calcium from the surface of the root portion 24 and also importantly to leave a residue of Tetracycline on the root portion 24. This Tetracycline residue retards undesired epithelial cell attachment to the surface of the root portion 24 and promotes connective tissue cell attachment to root portion 24.

During the chemical treatment of the surface of the root portion 24 illustrated in FIGS. 6 and 7, saliva contamination of the surface of the root portion 24 must be avoided using techniques known in the art. Otherwise, the chemical treatments may not be effective.

FIG. 8 illustrates the next step in the practice of the method of the invention and the use of the composition of the invention. In this step, the bony defect 43 is filled with the bone growth promoting composition 58. To fill the bony defect 43 an open ended 1 ml. syringe 60 is filled with the composition 58 and the open end portion 62 is placed adjacent the bony defect 43. Then the plunger 64 of the syringe 60 is pushed inward to expel the composition 58 from the syringe 60 and into the bony defect 43. The bony defect 43 is overfilled with the composition 58. To accomplish this overfilling, saliva 66 from the mouth and blood from the surrounding bone is allowed to come into contact with the composition 58 as the composition 58 is being placed into the bony defect 43. The saliva and blood activate the composition 58 and cause it to stick to itself and also to the treated surface of the root portion 24. This adhesion of the composition 58 to itself and to the treated root portion 24 surface permits the bony defect to be overfilled.

The next step in the practice of the method of the invention and in the use of the composition of the invention is illustrated in FIG. 9. As illustrated in FIG. 9, the sufficient composition 58 should be added to the bony defect pocket 43 in order that the outer surface 68 of the overfill of the composition 58 is substantially 3 millimeters above the adjacent edges 70 of the bony defect pocket 43. As illustrated in FIG. 9, after this filling the perpheral edges of the flaps 40 are sutured together in a manner well known in the art.

FIGS. 10 through 13 illustrate the healing process involved with the method of the invention and the use of the composition of the invention. As illustrated in FIG. 10, after approximately one week after the previously described surgery, the flap edges 40 die back over the composition 58, but this composition 58 limits the extent of the die back.

Figure 11:
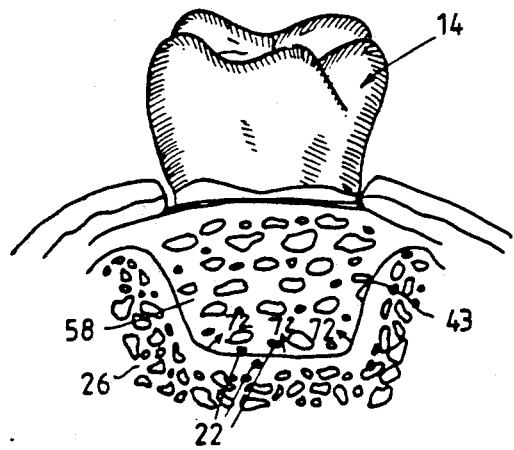
FIG. 11 is a sectional view of the structure set forth in FIGS. 2 through 10 illustrating a further step in the healing process associated with the practice of the method of the invention and the use of the composition of the invention.
Figure 12:
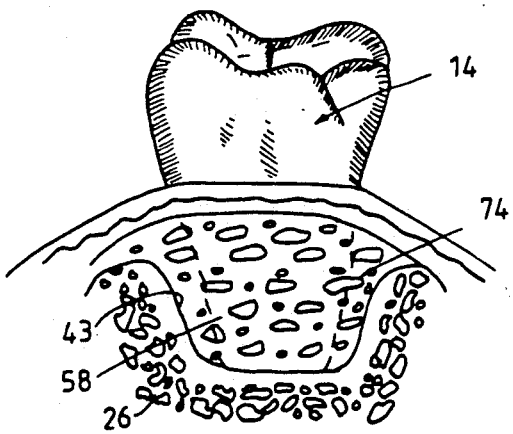
FIG. 12 is a sectional view of the structure set forth in FIGS. 2 through 11 illustrating a further step in the healing process associated with the practice of the method of the invention and the use of the composition of the invention.

FIG. 11 illustrates the healing process approximately one month after the previously described surgery. At this stage in the healing process cells represented by the number 22 from the bone 26 migrate into the composition 58 as represented by the arrows 72. Then as indicated in FIG. 12, three months after the previously described surgical proceedure, new bone 74 is noted in the area of the composition 58, the epithelial mono layer 76 thickens followed by the development of connective tissue thickening between the bone 26 and the epithelium. The composition 58 is fully colonized by osteoblasts.

Figure 13:
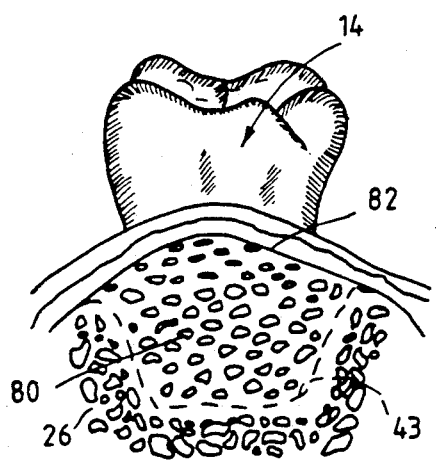
FIG. 13 is a sectional view of the structure set forth in FIGS. 2 through 12 illustrating a further step in the healing process associated with the practice of the method of the invention and the use of the composition of the invention.

FIG. 13 illustrates the healing process some six months to one year after the previously described surgical proceedure. It will be noted that the connective tissue interface has widened maximally and that the original bony crater or defect 43 is no longer present. Instead the same area is filled with new bone 80 that has a flat to slightly rounded outer surface 82. At this stage the healing process is essentially complete although bone maturation may continue for some one to two years that will show as increased density in the original bony defect 43 area on x-rays. At this point the method of the invention and the use of the composition 58 would normally be complete.

Figure 14:
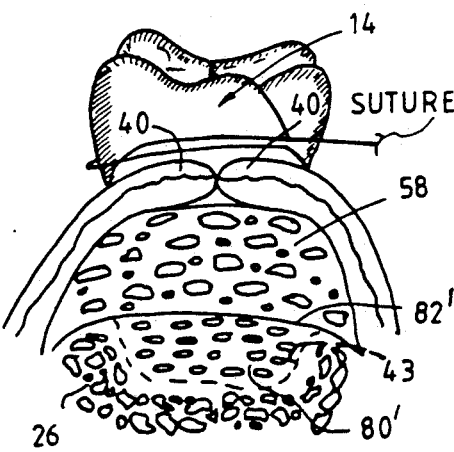
FIG. 14 is a sectional view of the structure set forth in FIGS. 2 through 13 illustrating the final step in the practice of the method of the invention and the use of the composition of the invention.

In some cases the bony defect 43 may be very deep and require extensive growth of new bone to fill it. In this case, further steps in the method are necessary. These steps are indicated in FIG. 14. As indicated in FIG. 14, it is possible to repeat the process previously described and set forth in FIGS. 2 through 9. In doing this the composition 58 is placed on top of the surface 82' of the previously grown new graft bone 80'. This can be performed from substantially six months to substantially one year after the initial previously described surgical procedure has been completed.

Figure 15:
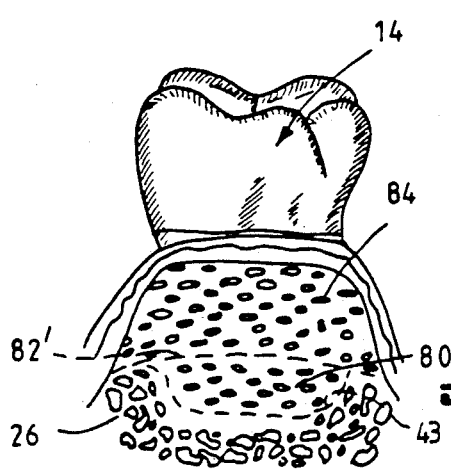
FIG. 15 is a sectional view of the structure set forth in FIGS. 2 through 14 illustrating the final result of the method and the use of the composition of the invention.

FIG. 15 illustrates how the graft area looks approximately one year after the second operation illustrated in FIG. 14. As indicated, a second outer layer of bone 84 is present above the outer surface 82 of the bone 80 resulting from the first procedure illustrated in FIGS. 2 through 9.

The citric acid solution used in the previously described method is a 1 M water solution. It appears that this 1 M citric acid solution accomplishes the following:
a. exposes root collagen,
b. denatures root cementum absorbed bacterial endotoxin,
c. removes the "smear layer" left by hand and rotary instruments after mechanical root preparation (scaling and root planing)
d. sterilizes root surfaces, and
e. denatures root collagen (hypothesis) making the roots more desirable for fibronectin seating.

The previously mentioned Tetracycline solution is a 1 mg./ml. water solution. The bone graft composition 58 used in the previously described method is as follows:
  Hydroxyapatite (20 to 40 mesh)- 1 gm
  Hydroxyapatite (40 to 60 mesh)-0.5 gm
  Freeze dried decalcified human bone-1gm
  Tetracycline-200 mg
  Fibronectin-aqueous solution (from 5 $\mu$g/ml to 50 $\mu$g/ml concentration)-3 ml These ingredients are thoroughly mixed prior to the composition 58 being used in the previously described method. This mixing must take place about a minimum of 15 minutes prior to use. An alternative embodiment for the bone graft composition 58 used in the previously described method is as follows:
  Hydroxyapatite (20 to 40 mesh)-1 gm.
  Hydroxyapatite (40 to 60 mesh)-0.5 gm.
  Collagen porous beads-250 to 800 micron diameter-1 gm.
  Tetracycline-50 to 200 gm.
  Aqueous solution-3 ml containing:
    Fibronectin FN-(5 $\mu$gm/ml to 50 $\mu$gm/ml);
    Bone Morphologic Protein-(0.1 ngm/ml to 5 ngm/ml);
    Fibroblast Growth factor (FGF) -(0.1 ngm/ml to 5 ngm/ml);
    Insulin-(0.5 $\mu$gm/ml to 8 $\mu$gm/ml);
    Absorbic Acid (vitamin C)-(0.5 $\mu$gm/ml to 15 $\mu$gm/ml);
    and Choline chloride-(5 $\mu$gm/ml to 80 $\mu$gm/ml).

These ingredients are thoroughly mixed prior to the composition 58 being used in the previously described method. This mixing must take place in a minimum of 15 minutes prior to use.

As far as is understood, the purposes of each of the components of the bone graft composition are as follows:
1. Freeze dried decalcified bone-FDDBA (Raw Bone Morphologic Protein BMP)

a. A source of raw collagen it acts as a hemostatic static agent by activating the extrinsic clotting system and provides surfaces on which cell migration and growth may occur. In the present preferred mixture collagen porous microcarriers are substituted as the source of collagen. These particles are essentially spherical with diameters of 250 to 800 microns. Scanning electron microscopy shows surface pores of about 20 microns and about 40 microns on the interior. The interior is made up of both fibrous and sheet-like structures, providing surfaces for cell attachment. The voids interconnect, providing access to the cells throughout the interior of the particle. When dry, porous microcarriers contain about 5 gm of collagen per liter of bead internal volume. One gram of hydrated microcarriers in phosphate buffered saline occupies a settled bed volume of about 250 ml. The material is roughly 99.5% void volume; this makes it very efficient in terms of the potential cell mass that can be grown per gram of microcarrier. When wetted with the previous aqueous solution, cell adhesion, propagation and resulting bone formation is promoted.

b. BMP attracts osteoblasts (chemotaxis) and stimulates them to secrete bone. Purified bone morphologic proteins have been extracted by methods known to the art. These extracted molecules act in substantially the same manner as the raw BMP to attract osteoblasts and stimulate them to secrete bone and so may be substituted for freeze dried decalcified bone. The amino acid sequence of one or more of these bone morphologic proteins proteins have been determined and by the process of recombinant DNA procedures bacteria have been induced to produce the BMP sequences. These recombinent products act in essentially the same manner as raw BMP so one may be substituted for freeze-dried decalcified bone.

2. HA (Hydroxyapatite)

a. Gives structural support to the graft mixture preventing collagen collapse resulting in residual defect formation post grafting. Two sizes of HA are used to create interparticulate interstices into which cells and blood vessels could grow. Commercial periodontal HA is too small and does not allow proper in growth.

b. Has a hydrophillic surface which reacts (absorbs or adheres) with the contents of the previous aqueous solution to promote cell adhesion, propagation and resulting bone formation.

c. Once coated or activated chemically each HA particle becomes a cell growth site.

d. Two sizes of HA are used 20–40 mesh and 40–60 mesh. Although a single size coralene HA with appropriate intertices may be alternatively used. The HA intertices created by the large particles are partially again filled by the smaller particles. The collagen and cells forming in these spaces and attached to the HA particle surfaces cannot contract as would normally occur.

e. Alternatively other calcified solids such as calcium carbonate, or rigid plastics such as teflon could be substituted for the hydroxyapatite as long as they are of the same mesh sizes.

3. Tetracycline a. Antibiotic effect (1) Graft material storage preservative.

(2) Direct antibacterial effect on oral plaque (bacteria) during wound healing, avoiding graft contamination.

(3) Long term slow release mechanism due to its biochemical affinity to bone prevents reinfection by bacteria of graft sites and eliminates deep bacterial contamination of the graft site.

b. Antimetabolite effect generally slows cell function during cell turn over. This is good as it restricts aberrant cell overgrowth. The Tetracycline in effect calms the cells down and has them produce product (bone and collagen) rather than just rapidly and destructively reproducing.

c. Tetracycline preferentially retards epithelial cell growth versus connective tissue cell growth. This effect plus the effect of the cortical bone factor yields an initial skin (epithelium) "die back" post surgery allowing connective tissue proliferation into the graft material. Tetracycline pretreatment of the roots slows epithelial repopulation and downgrowth and preferentially allows connective tissue cell growth and attachment.

d. Tetracycline in acid solution also acts to decalcify root surfaces.

4. Fibronectin (a cell attachment molecule)

a. Mediates cell to cell adhesion and attachment.

b. Mediates cell to substrate adhesion and attachment.

c. Orients fibroblasts to lay down collagen optimally in wound healing.

d. Has attachment sites for fibrin and heprin (main constituents of blood clots). Thus orients cells for proper healing.

e. As the graft mixture fluid (20% fibronectin) is the first chemical to touch the pretreated root surface. The fibronectin optimally allows fibrin attachment to the root surface a precursor to connective tissue reattachment.

f. Fibronectin attaches preferentially to denatured collagen such as that produced by the 1 ml citric acid root pre treatment.

g. Fibronectin when activated by glycoaminoglycans (GAG) in saliva cause jelling of all components treated by the fibronectin giving the graft material to an inherent "body" and an ability to stick to whatever surface it touches h. Other cell attachment molecules including vitronectin and cell spreading factor may be used in substitution or in addition to fibronectin.

5. Insulin a. Produced by the pancreas normally this hormone regulates intercellular carbohydrate metabolism throughout the body.

b. In the new preferred mixture insulin acts to counter the action interleukin II stimulation of osteoclasts (bone eating cells) and stimulates osteoblast activity.

c. It activates along with cGMP and rethenoic acid the regulatory codons on the chromosone encoded for collagen and bone formation to make bone and collagen.

6. Choline a. A precursor to acetylcholine and serotonin, Choline is an essential nutrient for cell growth and enhances cell secretion. It stabilizes cellular membranes after injury or infection. Via acetylcholine it increases intercellular cGMP levels.

7. Cell Growth Factors a. Numerous factors have been identified and purified. Growth factors can be used in conjunction with other essential nutrients to reduce or eliminate the need for other supplements. The following list includes:

(1) epidermal growth factor-EGF (2) fibroblast growth factor-FGF (3) platelet derived growth factor-PdGF
(4) periodontal ligament derived growth factor-PLDGF
(5) Insulin-like growth factor-IGF
Of the foregoing FGF is preferred.

8. Ascorbic Acid a. Ascordic acid is a co-enzyme in the formation of collagen. Supplements may increase collagen production by fibroblasts 2 to 3 fold above normal levels. Vitamin C elevates the steady state level of cGMP.

All working together, these ingredients of the bone graft composition 58 fill periodontal bony defects and allow supracrestal augmentation by giving cells a treated matrix into which they are attracted to grow, adhere and proliferate while simultaneously excluding epithelial downgrowth. They also effect direct cell product activity and control bacterial contamination both pre and post surgery and long term in grafted areas.

It has been determined that the previously described bone growing method can be enhanced by the addition of the final method step of orally administering or providing post surgical oral nutrients to the surgical bone graft patient after the completion of the last surgical step in the previously described bone growing method. These post surgical nutrients and the dosage are set forth below:

| Nutrient Type & Size | Dosage |
| --- | --- |
| 1 gm Vitamin C | Take 500 mg twice a day. |
| 1 gm Tryptophane | Take 1 gm. one to two times daily, particularly at bedtime. |
| .5 gm Choline | Take 2 gms the evening after the surgery. After that take 500 mg once a day. |
| 1 gm Calcium | Take 500 mg twice a day. |
| 400 mg Vitamin E | Take 400 mg once a day. |
| 900 mg Ornithine | Take 900 mg once a day. |
| 1200 mg Arginine | Take 1200 mg once a day |

The foregoing should be taken for a minimum of a one month period following surgery.

As far as it is understood, the purposes of the supplements are collectively designed to increase cGMP (cyclic guanosine monophosphate) ad decrease cyclic cAMP (cyclic adenosine monophosphate). Cyclic nucleotides are the genetic control chemicals of the cells cGMP promotes movement of motile mammalian cells (defense cells) and secretions by secretory cells (salivary, connective tissue, bone and glandular). cAMP is the inhibitor of function of these cells. One could say that in regard to healing, cyclic GMP provides the "go" signal and cyclic AMP provides the "stop".

(1) Vitamin C elevates the steady state level of cGMP. It is the necessary enzyme for fibroblasts to produce collagen.

(2) Vitamin E inhibits cGMP hydrolysis and promotes degradation of cAMP. It increases the rate of cellular repair following injury.

(3) Calcium maintains basal level of cGMP. It is the major mineral component of bone. It is also the catalyst for blood clotting. Calcium is involved with an enormous number of chemical reactions in the body.

(4) Choline is the precursor to -acetylcholine which elevates cGMP. Choline enhances secretion by cells and stabilizes cell membranes after injury or infection.

(5) Tryptophane is the precursor to serotonin which in turn activates acetylcholine which elevates cGMP. At 0.5 to 1.5 grams it promotes the relaxation healing phase. It makes immune cells less irritable to mitogens avoiding over reaction of these cells insuring normal, rapid healing.

(6) Ornithine and Arginine cause the pituitary gland to release growth hormones and are generally involved in cell growth and repair.

Collectively these nutrients counteract the effects of:
Tobacco-nicotine increase cAMP
Alcohol-stabilizes the enzymes which preferentially degrade cGMP
Stress-acts through adrenal release of endogenous steroid parathyroid which results in inhibition of accumulation of cGMP
Steroids -inhibits accumulation of cGMP
Bruxism -produces an anodic electrical current in bone causing an increase in intercellular cAMP.

The following suggested procedures though they are not essential to the practice of the method and the use of the composition 58, have been found to give good results and hence are recommended. The bone growing composition 58 should be prepared at least one-half hour prior to its use. This is accomplished by mixing the Fibronectin or aqueous solution with the rest of the bone growing composition.

It is recommended that the graft sites be prepared in the standard fashion for osseous graft procedures. A "modified Widman" papillary saving, or Takei type flap design is recommended. Osseous lesions are to be completely debrided of connective tissue and granulation tissue. Bone fenestration into walls of the defects is optional. Tooth roots should be prepared to thoroughly remove all bacteria, calculus, and bacterially affected or hypercalcified cementum.

The graft material composition 58 is loaded into the syringe 60 by tamping the open barrel of the syringe 60 into the mixed graft material 58. After injecting the material into the defect, it should be further packed in place. Additional material may be added as needed or desired. Attempt at supracrestal augmentation is encouraged.

As close to primary closure as reasonably possible is recommended using a verticle mattress papillary suturing technique in either an interrupted or continuous manner. Graft sites are to be covered for one week using a suitable periodontal dressing such as COE Pak, Zone, etc.. Repacking a second week may be done at the judgment of the practitioner.

The recommended post surgical hygiene maintenance sequence is as follows: first two visits at one month intervals, then two months, and then every three months. A plaque index is recommended to numerically document plaque levels and as a basis for prescription of antiplaque agents. Recommended post surgical medications are as follows: Tetracycline 250 mg QID×2 weeks, Motrin 400-600 mg QID×2 days. It is also recommended that the patient be given the antibiotic Tetracycline and Motrin or Tylenol for pain after surgery.

The foregoing bone growing method and the bone growing composition 58 have been used successfully on a large number of patients that needed bone regeneration next to their teeth. Using this bone growing method and the composition 58 resulting in only very minimal shrinkage of the flap height against the adjacent tooth. This can be traced to the good bony defect fill of the composition 58 and also the ability to pile up the composition 58. This method also promotes bone proliferation and cell growth of bone cells by retarding gingival connective tissue growth. This retardation takes place predominately during substantially the first three weeks after surgery.

The bone growing method and the use of the bone growing composition 58 have been previously described in connection with their use in the human mouth. However, with appropriate apparent modifications the method and composition 58 can be used in connection with other locations in connection with other locations in the human body and can also be used in non-human living creatures.

Although the invention has been described with reference to certain preferred embodiments, it will be understood that variations and modifications may be made within the spirit and scope of the invention as defined in the appended claims.

What is claimed is:

1. A method of promoting the growth of bone in a living creature comprising the steps of:
   a. providing a structural support material;
   b. providing a material having attachment means;
   c. providing a source of bone morphologic protein;
   d. providing a source of collagen;
   e. providing at least one material having cell growth means;
   f. mixing said structural support material, said attachment material, said source of bone morphologic protein, and said source of collagen to form a graft composition;
   g. surgically operating on the living creature to expose living bone;
   h. inserting said graft composition adjacent said living bone to treat said living bone after said living bone has been surgically exposed; and
   i. surgically covering said living bone and said adjacently located graft composition.

2. The method of promoting growth of bone of claim 1 wherein said step of providing a material having cell growth means comprises providing a cell growth stimulating material and a nutrient material for promoting cell growth.

3. The method of promoting growth of bone of claim 1 further comprising the step of administering a nutrient after the step of covering said living bone.

4. The method of promoting growth of bone of claim 3 wherein said nutrient comprises at least one amino acid.

5. The method of promoting growth of bone of claim 1 further comprising the step of increasing intercellular cGMP after the step of covering said living bone.

6. The method of promoting growth of bone of claim 5 whereby an ideal environment for cell growth is provided along with a rigid structure and stimulated cell growth through the use of inductive cell growth and attachment factors and the increase in cGMP.

7. The method of promoting growth of bone of claim 1 whereby said attachment means is absorbed on the surface of said structural support material.

8. A bone growing composition for encouraging the growth of bone comprising a structural support material comprising hydroxyapatite, tetracycline, a bone stimulating material comprising bone morphologic protein, a cell attachment molecule, porous collagen beads having a diameter between 250 microns and 800 microns, a cell growth factor and a cell nutrient.

9. The bone growing composition of claim 8 where said porous collagen beads have an interior with both fibrous and sheet-like structures.

10. The bone growing composition of claim 8 wherein said porous collagen beads have surface pores and interior pores and wherein the surface pores are smaller in size than the interior pores.

11. The bone growing composition of claim 10 wherein said porous collagen beads have surface pores of about 20 microns and interior pores of about 40 microns.

12. The bone growing composition of claim 8 wherein said hydroxyapatite comprises particles having a plurality of sizes.

13. The bone growing composition of claim 12 wherein the sizes of two of said plurality of sizes are between 20 to 40 mesh and between 40 to 60 mesh.

14. The bone growing composition of claim 8 wherein said cell attachment molecule comprises vitronectin.

15. The bone growing composition of claim 8 wherein said cell attachment molecule comprises fibronectin.

16. The bone growing composition of claim 15 wherein said fibronectin is present in an aqueous solution in a concentration between 5 $\mu$gm/ml and 50 $\mu$gm/ml.

17. The bone growing composition of claim 8 wherein said cell growth factor comprises a fibroblast growth factor.

18. The bone growing composition of claim 8 wherein said cell growth factor comprises an insulin like growth factor.

19. The bone growing composition of claim 8 wherein said cell nutrient comprises choline.

20. The bone growing composition of claim 8 where said cell nutrient comprises ascorbic acid.

21. The bone growing composition of claim 8 wherein said composition includes an aqueous solution and wherein said cell attachment molecule, growth factor, and nutrient are located in said aqueous solution.

* * * * *